(12) United States Patent
Newton et al.

(10) Patent No.: US 6,339,042 B1
(45) Date of Patent: Jan. 15, 2002

(54) HERBICIDAL N-CYCLOHEXADIENYL HETEROARYLOXYACETAMIDES

(75) Inventors: Trevor Newton, Schwabenheim; Helmut Siegfried Baltruschat, Schweppenhausen, both of (DE)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/450,188

(22) Filed: Nov. 29, 1999

(51) Int. Cl.⁷ .............................................. A01N 57/18
(52) U.S. Cl. ..................... 504/202; 504/203; 504/263; 548/136; 548/221; 564/267
(58) Field of Search .............. 548/130, 221; 504/202, 263; 564/267

(56) References Cited

U.S. PATENT DOCUMENTS

| | | |
|---|---|---|
| 4,509,971 A | 4/1985 | Forster et al. |
| 4,585,471 A | 4/1986 | Forster et al. .................. 7/90 |
| 4,833,243 A | 5/1989 | Forster et al. |
| 5,101,034 A | 3/1992 | Schmidt et al. ............. 548/136 |

FOREIGN PATENT DOCUMENTS

| | | | |
|---|---|---|---|
| EP | 123996 | * 11/1984 | ................. 548/136 |
| WO | WO 97/08160 | 3/1997 | |
| WO | WO 99/25702 | 5/1999 | |

\* cited by examiner

*Primary Examiner*—Robert Gerstl
(74) *Attorney, Agent, or Firm*—Barbara V. Maurer

(57) ABSTRACT

The novel compounds of formula I:

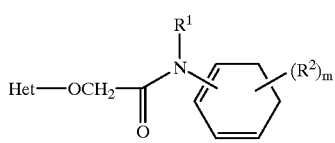

wherein

Het represents an optionally substituted, optionally benzofused nitrogen containing 5- or 6-membered heteroaromatic group;

$R^1$ represents an alkyl, alkoxyalkyl or cycloalkyl group;

$R^2$ each independently represent an alkyl or alkenyl group, and m is 0 or an integer from 1 to 6, and herbicidal compositions containing such compounds as active ingredients can be utilized in various agricultural methods.

16 Claims, No Drawings

HERBICIDAL N-CYCLOHEXADIENYL HETEROARYLOXYACETAMIDES

BACKGROUND OF THE INVENTION

This invention relates to certain novel heteroaryloxyacetic acid N-alkenylamides, to the preparation of such compounds, to herbicidal compositions containing such compounds, and to a method of combating undesired plant growth using such compounds.

U.S. Pat. No. 4,585,471 discloses, for example, a compound of formula

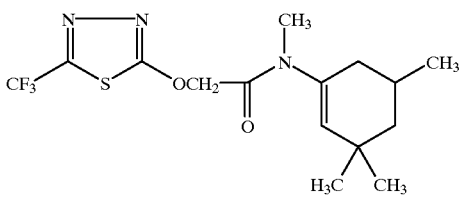

which are useful as herbicides.

European patent application EP 0 005 501 discloses herbicidal benzofused oxazol-2-yl- and thiazol-2-yl-oxyacetamides, in which the amido nitrogen atom is substituted by hydrogen atoms and/or by optionally substituted alkyl, alkenyl, alkynyl, aralkyl, cycloalkyl or aryl groups.

European patent application EP 0 165 537 discloses a process for the preparation of benzofused oxazol-2-yl- and thiazol-2-yl-oxyacetamides, in which the amido nitrogen atom is substituted by one or two allyl groups, one cyclohex-1-enyl, one cyclohex-3-enyl or one vinyl group. The compounds are taught to be useful as herbicidal agents.

International Patent Aplication WO 97/08160 discloses N-(1-isopropyl-2-methyl-1-propenyl)-heteroaryloxyacetamides, useful as herbicides.

International Patent Application WO 99/25702 discloses herbicidal heteroaryloxyacetamides, in which the amido nitrogen atom is substituted by a cyclohexenyl group.

However, none of these references disclose heteroaromatic oxyacetamides in which the amido nitrogen atom is attached to a cyclohexadienyl moiety.

Although many of the known heteroaryloxyacetamides show considerable activity against various weeds, they suffer from disadvantages due to their lack of selectivity or because of their undesirable persistence in the environment. The N-3,3,5-trimethylcyclohexadienyl heteroaryloxyacetamides of the present invention overcome these disadvantages, and also have the advantage of being obtainable from the ready available isophorone starting material. The compounds according to the present invention combine high herbicidal activity with the necessary selectivity and enhanced soil degradation.

SUMMARY OF THE INVENTION

The present invention relates to the novel compounds of the formula I

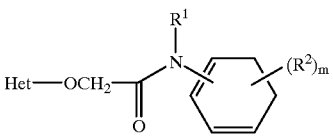

wherein

Het represents an optionally substituted, optionally benzofused nitrogen containing 5- or 6-membered heteroaromatic group;

$R^1$ represents an alkyl, alkoxyalkyl or cycloalkyl group;

$R^2$ each independently represent an alkyl or alkenyl group, and m represents 0 or an integer from 1 to 6.

Accordingly, the present invention provides novel compounds of formula I, methods for controlling undesired plant growth by contacting said plants with a herbicidally effective amount of the new compounds, selective herbicidal compositions containing the new compounds as active ingredients, and new processes for the preparation of the aforesaid novel compounds.

These compounds show excellent herbicidal activity at low dosages combined with higher selectivity in crops than those disclosed in the aforementioned prior act patent applications. They show an excellent selective herbicidal activity in certain crops, such as rice, maize, cereals, soybeans, sugarbeets, canola, sunflowers or potatoes, and enhanced soil degradation.

These and other objects and features of the invention will become more apparent from the detailed description set forth hereinbelow.

DETAILED DESCRIPTION OF THE PREFERRED EMBODIMENTS

It has surprisingly been found that the novel compounds of formula I show an excellent herbicidal activity against a broad range of weeds and exhibit a high degree of selectivity.

The term "optionally benzofused nitrogen containing 5- or 6-membered heteroaromatic group" means heteroaryl groups wherein the heteroatom or atoms are one to three nitrogen, oxygen or sulfur atoms, and includes azoles, such as pyrrole, pyrazole, and imidazole, oxazoles, thiazoles, thiadiazoles, azines such as pyridine, pyrimidine, pyrazine, pyridazine and triazines. Optionally benzofused azoles are preferred. Het preferably represents a thiadiazolyl, benzoxazolyl or benzthiazolyl group which may be substituted by one or more halogen atoms or alkyl, haloalkyl or phenyl groups.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules.

In relation to moieties defined above as comprising an optionally substituted heteroaryl group, such optional substituents include halogen, especially fluorine, chlorine and bromine atoms, and nitro, cyano, amino, hydroxyl, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkylthio and aryl groups such as phenyl. one to five substituents may be employed, with one or two substituents being preferred and one substituent being most preferred.

Het preferably represents a group selected from the formulae (1) and (2)

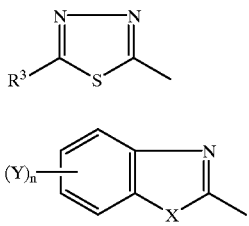

(1)

(2)

in which
R³ represents a hydrogen or halogen atom or an alkyl or haloalkyl group; preferably a $C_{1-4}$ alkyl or $C_{1-4}$ fluoroalkyl group, in particular a trifluoromethyl group X represents O or S;

Y represents independently of each other a halogen atom or an optionally substituted alkyl group, preferably a fluoro or chloro atom or a $C_{1-4}$ alkyl, $C_{1-4}$ fluoroalkyl, $C_{1-4}$ alkoxy or $C_{1-4}$ fluoroalkoxy group, and particularly, a chloro atom or methyl atom; and n is an integer from 0 to 4, preferably 0 or 1.

The thiadiazole derivatives (1) and the benzoxazole derivatives (2) of formula I wherein X is an oxygen atom are particularly preferred.

Generally, if any of the above mentioned moieties comprises an alkyl or alkenyl group, such groups, unless otherwise specified, may be linear or branched and may contain up to 6, preferably 1 to 4, carbon atoms. Examples of such alkyl or alkenyl groups are methyl, ethyl, propyl, (1)-butyl, isobutyl, tertiary-butyl and prop-1-en-2-yl groups. The alkyl portion of a haloalkyl, haloalkoxy, haloalkylthio, alkylthio or alkoxy group suitably has from 1 to 4 carbon atoms, preferably 1 or 2 carbon atoms.

Generally, if any of the above mentioned moieties comprises an alkoxyalkyl group, such groups, unless otherwise specified, may be linear or branched and may contain 2 to 12, preferably 3 to 5, carbon atoms. Examples of such groups are methoxymethyl, 2-methoxyethyl, 3-methoxypropyl, 2-methoxy-1-methylethyl and methoxybutyl.

"Halogen" means a fluorine, chlorine, bromine or iodine atom, and preferably is a fluorine, chlorine or bromine substitute.

Generally, if any of the above mentioned moieties comprises a haloalkyl group, such groups, unless otherwise specified, may be linear or branched and may contain 1 to 6, preferably 1 to 4, carbon atoms. Examples of such groups are halomethyl, haloethyl, halopropyl, haloisopropyl, halobutyl, haloisobutyl and halotertiary-butyl groups. Haloalkyl moieties of any groups within the definitions used herein can contain one or more halogen atoms, preferably fluorine, chlorine or bromine. Haloalkyl represents preferably mono-, di-, tri- or perfluoroalkyl groups, especially trifluoromethyl, pentafluoroethyl, 2,2,2-trifluoroethyl or 1,1,1-trifluoroprop-2-yl groups, with trifluoromethyl being the most preferred.

$R^1$ preferably represents $C_{1-4}$ alkyl, $C_{1-6}$ alkoxy-$C_{1-6}$-alkyl or $C_{3-7}$ cycloalkyl group with methyl, ethyl, propyl, isopropyl, cyclopropyl and 2-methoxyethyl groups being most preferred.

$R^2$ preferably each independently represent a $C_{1-4}$ alkyl or $C_{2-4}$ alkenyl group, and most preferably, a methyl group or prop-1-en-2-yl group. The m variable is preferably 1, 2 or 3, and most preferably is 3.

Particularly preferred are the compounds of formula IA,

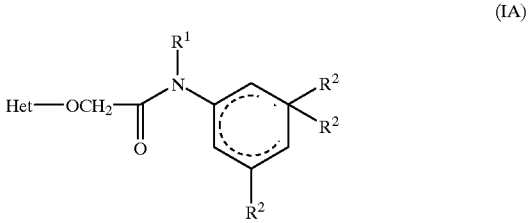

(IA)

wherein Het, $R^1$ and $R^2$ are as hereinbefore defined and the dashed line indicates the presence of two conjugated double bonds in one or the other position with respect to the point of attachment of the nitrogen atom.

Particularly preferred are the compounds selected from formulae IA1 and IA2,

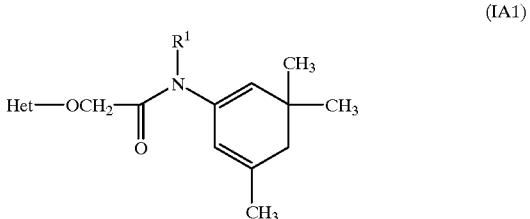

(IA1)

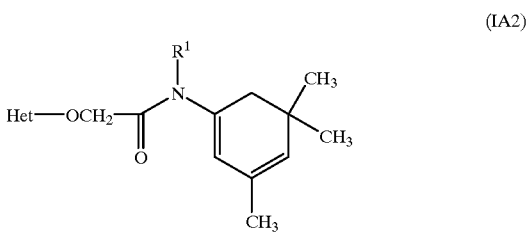

(IA2)

wherein
$R^1$ represents an alkyl or alkoxyalkyl group,
Het represents a group selected from the formulae (1) and (2)

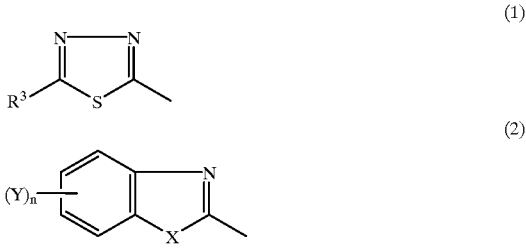

(1)

(2)

in which X represents O or S, and
Y represents a halogen atom or a methyl group,
n is 0 or 1, and
$R^3$ represents a $C_{1-4}$ alkyl or $C_{1-4}$ fluoroalkyl group.

The compounds of formula I can be prepared and used as an isomeric mixture of compounds of formula IA which differ only in the location of the conjugated double bond. Therefore, the invention preferably relates to a mixture of isomeric compounds of formula I which differ only in the location of the double bond, in particular, a mixture of the compounds of formula IA. Most preferred is a mixture of IA1 and IA2, wherein IA1 is the major component.

Representative of the invention are the following specific compounds:

2-(5-trifluoromethyl-[1,3,4]-thiadiazol-2-yloxy)-N-methyl-N-(3,5,5-trimethylcyclohexa-1,3-dienyl)-acetamide,
2-(5-trifluoromethyl-[1,3,4]-thiadiazol-2-yloxy)-N-ethyl-N-(3,5,5-trimethylcyclohexa-1,3-dienyl)-acetamide,
2-(5-trifluoromethyl-[1,3,4]-thiadiazol-2-yloxy)-N-methyl-N-(3,3,5-trimethylcyclohexa-1,5-dienyl)-acetamide,
2-(5-trifluoromethyl-[1,3,4]-thiadiazol-2-yloxy)-N-ethyl-N-(3,3,5-trimethylcyclohexa-1,5-dienyl)-acetamide, 2-(5-ethyl-[1,3,4]-thiadiazol-2-yloxy)-N-methyl-N-(3,5,5-trimethylcyclohexa-1,3-dienyl)-acetamide,
2-(5-ethyl-[1,3,4]-thiadiazol-2-yloxy)-N-ethyl-N-(3,5,5-trimethylcyclohexa-1,3-dienyl)-acetamide,
2-(5-ethyl-[1,3,4]-thiadiazol-2-yloxy)-N-methyl-N-(3,3,5-trimethylcyclohexa-1,5-dienyl)-acetamide,
2-(5-ethyl-[1,3,4]-thiadiazol-2-yloxy)-N-ethyl-N-(3,3,5-trimethylcyclohexa-1,5-dienyl)-acetamide, 2-(5-pentafluoroethyl-[1,3,4]-thiadiazol-2-yloxy)-N-methyl-N-(3,5,5-trimethylcyclohexa-1,3-dienyl)-acetamide,
2-(5-pentafluoroethyl-[1,3,4]-thiadiazol-2-yloxy)-N-ethyl-N-(3,5,5-trimethylcyclohexa-1,3-dienyl)-acetamide,
2-(5-pentafluoroethyl-[1,3,4]-thiadiazol-2-yloxy)-N-methyl-N-(3,3,5-trimethylcyclohexa-1,5-dienyl)-acetamide,
2-(5-pentafluoroethyl-[1,3,4]-thiadiazol-2-yloxy)-N-ethyl-N-(3,3,5-trimethylcyclohexa-1,5-dienyl)-acetamide,
2-(5-tert-butyl-[1,3,4]-thiadiazol-2-yloxy)-N-methyl-N-(3,5,5-trimethylcyclohexa-1,3-dienyl)-acetamide,
2-(5-tert-butyl-[1,3,4]-thiadiazol-2-yloxy)-N-ethyl-N-(3,5,5-trimethylcyclohexa-1,3-dienyl)-acetamide,
2-(5-tert-butyl-[1,3,4]-thiadiazol-2-yloxy)-N-methyl-N-(3,3,5-trimethylcyclohexa-1,5-dienyl)-acetamide,
2-(5-tert-butyl-[1,3,4]-thiadiazol-2-yloxy)-N-ethyl-N-(3,3,5-trimethylcyclohexa-1,5-dienyl)-acetamide,
2-(5-trifluoromethyl-[1,3,4]-thiadiazol-2-yloxy)-N-isopropyl-N-(3,5,5-trimethylcyclohexa-1,3-dienyl)-acetamide,
2-(5-trifluoromethyl-[1,3,4]-thiadiazol-2-yloxy)-N-isopropyl-N-(3,3,5-trimethylcyclohexa-1,5-dienyl)-acetamide,
2-(5-ethyl-[1,3,4]-thiadiazol-2-yloxy)-N-isopropyl-N-(3,5,5-trimethylcyclohexa-1,3-dienyl)-acetamide,
2-(5-ethyl-[1,3,4]-thiadiazol-2-yloxy)-N-isopropyl-N-(3,3,5-trimethylcyclohexa-1,5-dienyl)-acetamide,
2-(5-pentafluoroethyl-[1,3,4]-thiadiazol-2-yloxy)-N-isopropyl-N-(3,5,5-trimethylcyclohexa-1,3-dienyl)-acetamide,
2-(5-pentafluoroethyl-[1,3,4]-thiadiazol-2-yloxy)-N-isopropyl-N-(3,3,5-trimethylcyclohexa-1,5-dienyl)-acetamide,
2-(5-tert-butyl-[1,3,4]-thiadiazol-2-yloxy)-N-isopropyl-N-(3,5,5-trimethylcyclohexa-1,3-dienyl)-acetamide,
2-(5-tert-butyl-[1,3,4]-thiadiazol-2-yloxy)-N-isopropyl-N-(3,3,5-trimethylcyclohexa-1,5-dienyl)-acetamide,
2-(5-trifluoromethyl-[1,3,4]-thiadiazol-2-yloxy)-N-(2-methoxyethyl)-N-(3,5,5-trimethylcyclohexa-1,3-dienyl)-acetamide,
2-(5-trifluoromethyl-[1,3,4]-thiadiazol-2-yloxy)-N-(2-methoxyethyl)-N-(3,3,5-trimethylcyclohexa-1,5-dienyl)-acetamide,
2-(5-trifluoromethyl-[1,3,4]-thiadiazol-2-yloxy)-N-cyclopropyl-N-(3,5,5-trimethylcyclohexa-1,3-dienyl)-acetamide,
2-(5-trifluoromethyl-[1,3,4]-thiadiazol-2-yloxy)-N-cyclopropyl-N-(3,3,5-trimethylcyclohexa-1,5-dienyl)-acetamide,
2-(benzoxazol-2-yloxy)-N-methyl-N-(3,5,5-trimethylcyclohexa-1,3-dienyl)-acetamide,
2-(benzoxazol-2-yloxy)-N-methyl-N-(3,3,5-trimethylcyclohexa-1,5-dienyl)-acetamide,
2-(benzoxazol-2-yloxy)-N-ethyl-N-(3,5,5-trimethylcyclohexa-1,3-dienyl)-acetamide,
2-(benzoxazol-2-yloxy)-N-ethyl-N-(3,3,5-trimethylcyclohexa-1,5-dienyl)-acetamide,
2-(benzoxazol-2-yloxy)-N-isopropyl-N-(3,5,5-trimethylcyclohexa-1,3-dienyl)-acetamide,
2-(benzoxazol-2-yloxy)-N-isopropyl-N-(3,3,5-trimethylcyclohexa-1,5-dienyl)-acetamide,
2-(benzoxazol-2-yloxy)-N-(2-methoxyethyl)-N-(3,5,5-trimethylcyclohexa-1,3-dienyl)-acetamide,
2-(benzoxazol-2-yloxy)-N-(2-methoxyethyl)-N-(3,3,5-trimethylcyclohexa-1,5-dienyl)-acetamide,
2-(5-chloro-benzoxazol-2-yloxy)-N-methyl-N-(3,5,5-trimethylcyclohexa-1,3-dienyl)-acetamide,
2-(5-chloro-benzoxazol-2-yloxy)-N-methyl-N-(3,3,5-trimethylcyclohexa-1,5-dienyl)-acetamide,
2-(5-chloro-benzoxazol-2-yloxy)-N-ethyl-N-(3,5,5-trimethylcyclohexa-1,3-dienyl)-acetamide,
2-(5-chloro-benzoxazol-2-yloxy)-N-ethyl-N-(3,3,5-trimethylcyclohexa-1,5-dienyl)-acetamide,
2-(5-chloro-benzoxazol-2-yloxy)-N-isopropyl-N-(3,5,5-trimethylcyclohexa-1,3-dienyl)-acetamide,
2-(5-chloro-benzoxazol-2-yloxy)-N-isopropyl-N-(3,3,5-trimethylcyclohexa-1,5-dienyl)-acetamide,
2-(6-chloro-benzoxazol-2-yloxy)-N-methyl-N-(3,5,5-trimethylcyclohexa-1,3-dienyl)-acetamide,
2-(6-chloro-benzoxazol-2-yloxy)-N-methyl-N-(3,3,5-trimethylcyclohexa-1,5-dienyl)-acetamide,
2-(6-chloro-benzoxazol-2-yloxy)-N-ethyl-N-(3,5,5-trimethylcyclohexa-1,3-dienyl)-acetamide,
2-(6-chloro-benzoxazol-2-yloxy)-N-ethyl-N-(3,3,5-trimethylcyclohexa-1,5-dienyl)-acetamide,
2-(benzoxazol-2-yloxy)-N-isopropyl-N-(3,5,5-trimethylcyclohexa-1,3-dienyl)-acetamide,
2-(6-chloro-benzoxazol-2-yloxy)-N-isopropyl-N-(3,5,5-trimethylcyclohexa-1,3-dienyl)-acetamide,
2-(5-chloro-benzoxazol-2-yloxy)-N-(2-methoxyethyl)-N-(3,5,5-trimethylcyclohexa-1,3-dienyl)-acetamide,
2-(5-chloro-benzoxazol-2-yloxy)-N-(2-methoxyethyl)-N-(3,3,5-trimethylcyclohexa-1,5-dienyl)-acetamide,
2-(6-chloro-benzoxazol-2-yloxy)-N-(2-methoxyethyl)-N-(3,5,5-trimethylcyclohexa-1,3-dienyl)-acetamide,
2-(6-chloro-benzoxazol-2-yloxy)-N-(2-methoxyethyl)-N-(3,3,5-trimethylcyclohexa-1,5-dienyl)-acetamide,
2-(5-methyl-benzoxazol-2-yloxy)-N-methyl-N-(3,5,5-trimethylcyclohexa-1,3-dienyl)-acetamide,
2-(5-methyl-benzoxazol-2-yloxy)-N-methyl-N-(3,3,5-trimethylcyclohexa-1,5-dienyl)-acetamide,
2-(5-methyl-benzoxazol-2-yloxy)-N-ethyl-N-(3,5,5-trimethylcyclohexa-1,3-dienyl)-acetamide,
2-(5-methyl-benzoxazol-2-yloxy)-N-ethyl-N-(3,3,5-trimethylcyclohexa-1,5-dienyl)-acetamide,
2-(5-methyl-benzoxazol-2-yloxy)-N-isopropyl-N-(3,5,5-trimethylcyclohexa-1,3-dienyl)-acetamide,
2-(5-methyl-benzoxazol-2-yloxy)-N-isopropyl-N-(3,3,5-trimethylcyclohexa-1,5-dienyl)-acetamide,
2-(5-methyl-benzoxazol-2-yloxy)-N-(2-methoxyethyl)-N-(3,5,5-trimethylcyclohexa-1,3-dienyl)-acetamide, 2-(5-methyl-benzoxazol-2-yloxy)-N-(2-methoxyethyl)-N-(3,3,5-trimethylcyclohexa-1,5-dienyl)-acetamide,
2-(benzothiazol-2-yloxy)-N-methyl-N-(3,5,5-trimethylcyclohexa-1,3-dienyl)-acetamide,
2-(benzothiazol-2-yloxy)-N-methyl-N-(3,3,5-trimethylcyclohexa-1,5-enyl)-acetamide,
2-(benzothiazol-2-yloxy)-N-ethyl-N-(3,5,5-trimethylcyclohexa-1,3-dienyl)-acetamide,
2-(benzothiazol-2-yloxy)-N-ethyl-N-(3,3,5-trimethylcyclohexa-1,5-enyl)-acetamide,
2-(benzothiazol-2-yloxy)-N-isopropyl-N-(3,5,5-trimethylcyclohexa-1,3-dienyl)-acetamide,
2-(benzothiazol-2-yloxy)-N-isopropyl-N-(3,3,5-trimethylcyclohexa-1,5-dienyl)-acetamide,
2-(benzothiazol-2-yloxy)-N-(2-methoxyethyl)-N-(3,5,5-trimethylcyclohexa-1,3-dienyl)-acetamide,
2-(benzothiazol-2-yloxy)-N-(2-methoxyethyl)-N-(3,3,5-trimethylcyclohexa-1,5-dienyl)-acetamide.

The compounds of formula I are oils, gums, or crystalline solid materials. They are superior by virtue of their valuable herbicidal properties. For example, they can be used in agriculture or related fields for the control of undesired vegetation. The compounds of general formula I according to the invention possess a high herbicidal activity within a wide concentration range and at low dosages, and may be used in agriculture without any difficulties, in particular, for the selective control of undesired plants such as *Alopecurus myosuroides, Echinochloa crus-galli, Setaria viridis, Galium aparine, Stellaria media, Veronica persica, Digitaria sanguinalis, Lolium perenne, Lamium purpureum, Viola arvensis, Abutilon theophrasti, Ipomoea purpurea* and *Amaranthus retroflexus* by pre- and post-emergence application, particularly in certain crops, such as maize and rice.

The compounds according to the invention can be prepared by conventional methods.

A suitable process for the preparation of the compounds of general formula I comprises the reaction of a compound of formula II:

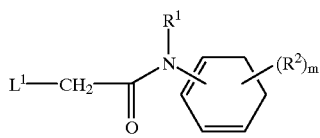
(II)

in which $R^1$, $R^2$ and m are as hereinbefore defined with a compound of general formula III,

Het—$L^2$  (III)

in which Het is as hereinbefore defined, and one of $L^1$ and $L^2$ represents a hydroxy group and the other represents a leaving group.

The reactions may be carried out in the absence or presence of a solvent which promotes the reaction or at least does not interfere with it. Preferred are polar, aprotic or protic solvents, such as N,N-dimethylformamide, dimethylsulfoxide, sulfolane, acetone, acetonitrile, methyl ethyl ketone, or an ether, such as tetrahydrofuran or dioxane, or alcohols, or water, or mixtures thereof. The reaction is carried out at a temperature between ambient temperature and the reflux temperature of the reaction mixture, preferably at elevated temperature, and especially at reflux temperature. Conveniently, substantially equimolar amounts of reactants are used.

The reaction may be carried out in the presence of a basic compound such as an alkali hydroxide, bicarbonate or carbonate, e.g., sodium or potassium hydroxide, bicarbonate or carbonate, an alkali alkoxide, e.g., sodium ethoxide, or an organic base such as triethylamine. In a particularly preferred embodiment, the process according to the invention is carried out in the presence of a phase transfer catalyst, preferably a tetraalkyl-ammonium halide, in particular tetraethyl-ammonium bromide.

Suitable leaving groups $L^1$ or $L^2$, respectively, are these such as alkyl- and arylsulfonyl, in particular methylsulfonyl, alkyl- and arylsulfonyloxy or perfluoroalkylsulfonyloxy groups and halogen atoms, particularly fluorine, chlorine and bromine.

The compounds used as starting material are partly known and partly novel. The present invention also relates to the novel intermediates, in particular to the compounds of formula II,

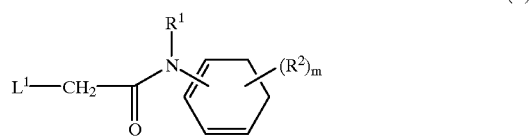
(II)

in which $R^1$, $R^2$ and m are as hereinbefore defined and $L^1$ represents a hydroxy group or a leaving group selected from alkyl- and arylsulfonyl, alkyl- and arylsulfonyloxy, perfluoroalkylsulfonyloxy groups and halogen atoms.

Most preferred compounds of the invention are those of formula IIA

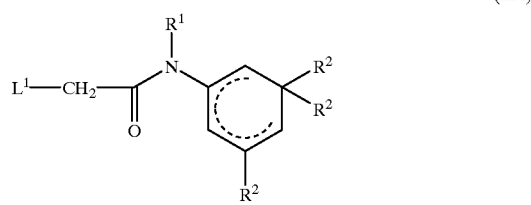
(IIA)

wherein
$R^1$ represents an alkyl, cycloalkyl or alkoxyalkyl group,
$L^1$ represents a hydroxy group or a halogen atom, and the curved line indicates the presence of two conjugated double bonds in one or the other position with respect to the point of attachment of the nitrogen atom.

The compounds of formula II are obtained from the corresponding cyclohexenimines of formula IV

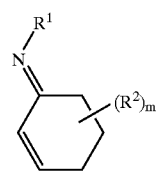
(IV)

wherein $R^1$, $R^2$ and m are as defined in formula I, by reaction with 2-chloroacetyl chloride and subsequent reaction with alkali acetate, or directly by reaction with 2-acetoxyacetyl chloride and deacylation with an aqueous alcoholic alkali hydroxide solution.

The imines of formula IV can be prepared by condensation of a primary amine and the corresponding cyclohexenone. When unsymmetrical ketones are used, the resulting double bond in the corresponding compounds of formulae I and II can be formed in two different positions. The reaction product then can contain a mixture of isomeric compounds of formulae I or II which differ only in the location of the conjugated double bonds. Cyclohexenones, which are readily commercially available such as cyclohex-2-enone, 3-methylcyclohex-2-enone, carvone and 3,5,5-trimethylcyclohexa-2-enone (isophorone), are preferred starting materials with Isophorone being most preferred. The condensation reaction between the cyclohexenone and the amine can be carried out by known procedures, such as by removing the product water by azeotropic distillation. The elimination of the water may be accelerated by addition of acid or acid catalysts, such as hydrochloric acid, paratoluenesulfonic acid or ammonium sulfate, or basic compounds such as sodium or potassium hydroxide, and alkali carbonates, or by dehydrating agents such as $TiCl_4$ or molecular sieves. In a preferred process for the preparation of the imines of formula IV the cyclohexenone is treated with a mixture of a primary alkylamine in the presence of the corresponding alkylammonium halide and subsequently treated with a basic compound, most preferably, potassium hydroxide.

The present invention also concerns the methods of using the compounds of formula I as herbicides. Thus, this invention provides a method of combating undesired plant growth at a locus by treating the locus with a herbicidally effective amount of a compound of formula I, typically incorporated into a herbicidal composition.

Particularly interesting activity has been found against grasses and broad leaf weeds, both pre- and post-emergence. Selectivity in important crop species such as wheat, barley, maize, rice and soybeans has also been found. As a useful action is by foliar spray application, the locus is most suitably the plants in a crop area, typical crops being cereals, maize, soybeans, sunflower or cotton. However, application may also be to the soil for those compounds having pre-emergence herbicidal action, or to the water, e.g., for crops such as paddy rice. The herbicidally effective amount of active ingredient used may, for example be in the range of from 0.005 to 3 kg/ha, preferably 0.01 to 1 kg/ha.

The present invention further provides a herbicidal composition which comprises an active ingredient, which is at least one compound of formula I as defined above, and one or more carriers. Preferably, at least one of the carriers is a surface active agent. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers in order to broaden the scope of herbicidal activity of the composition.

A composition according to the invention preferably contains from 0.5% to 95% by weight (w/w) of one or more active ingredients.

An agronomically acceptable carrier in a composition according to the invention is any material with which the active ingredient can be formulated to facilitate application to the locus to be treated, which may, for example, be a plant, seed or soil, or to facilitate storage, transport or handling. The carrier may be solid or liquid, and includes material which is normally a gas but which has been compressed to form a liquid.

The compositions may be manufactured into, e.g. emulsions concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally, solid and/or liquid auxiliaries and/or adjuvants. The form of the application, such as spraying, atomizing, dispersing or pouring, can be chosen in accordance with the desired objectives and the given circumstances of application.

The solvents utilized may be aromatic hydrocarbons, e.g. Solvesso® 200, substituted naphthalenes, phthalic acid esters, e.g., dibutyl or dioctyl phthalate, aliphatic hydrocarbons, e.g., cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different solvents are often suitable as carriers.

Solid carriers, which may be used for dusts, wettable powders, water dispersible granules, or granules, can be mineral fillers, such as calcite, talc, kaolin, montmorillonite or attapulgite. The physical properties may be improved by addition of highly dispersed silica gel or polymers. Carriers for granules can be porous material, e.g., pumice, kaolin, sepiolite, bentonite; non-sorptive carriers may be calcite or sand. Additionally, a multitude of pre-granulated inorganic or organic materials can be used, such as dolomite or crushed plant residues.

Herbicidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

The surfactants utilized can be nonionic, anionic, cationic or zwitterionic substances with good dispersing, emulsifying and wetting properties depending on the nature of the particular compound of formula I to be formulated. The term "surfactants" is also intended to encompass mixtures of two or more surfactants.

The compositions of the invention may, for example, be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain, in addition to a solid inert carrier, 3 to 10% w/w of dispersing and wetting agents and, where necessary, 0 to 10% w/w of stabilizer(s) and/or other additives such as penetrants or retention enhancers (stickers). Dusts are usually formulated as a dust concentrate having a similar composition to that of a wettable powder but without a dispersant, and may be diluted in the field with a further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives, such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and retention enhancers (stickers), and water or an organic liquid in which the active ingredient is substantially insoluble. Certain organic solids or inorganic salts may be present dissolved in the formulation to assist in preventing sedimentation and crystallization, or as anti-freeze agents, in the case of water.

Aqueous dispersions and emulsions, for example, compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity, the compositions are preferably in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
| --- | --- | --- |
| Active Ingredient | Compound of Example 1 | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |
| Suspension Concentrate (SC) | | |
| Active Ingredient | Compound of Example 1 | 50% (w/v) |
| Dispersing agent | Soprophor ® FL[3] (polyoxyethyiene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Keizan ® S[4] (Xanthan gum) | 0.2% (w/v) |
| Antifreezing agent | Propylene glycol | 5% (w/v) |

| -continued | | |
| --- | --- | --- |
| Biocidal agent | Proxel ®[5] (aqueous dipropylene glycol solution containing 20% 1,2-benisothiazolin-3-one) | 0.1% (w/v) |
| Water | | to 1000 ml |
| Wettable Powder (WP) | | |
| Active ingredient | Compound of Example 2 | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates | 3% (w/w) |
| Carrier/Filler | Kaolin | 35% (w/w) |
| Water Dispersible Granules (WG) | | |
| Active Ingredient | Compound of Example 2 | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Kaolin | 35% (w/w) |

[1] commercially available from ICI Surfactants
[2] commercially available from Deutsche Shell AG
[3] commercially available from Rhone-Poulenc
[4] commercially available from Kelco Co.
[5] commercially available from Zeneca
[6] commercially available from Witco
[7] commercially available from International Speciality Products The compositions of this invention can also comprise other compounds having biological activity, e.g., compounds having similar or complementary pesticidal activity or compounds having plant growth regulating, fungicidal or insecticidal activity. These mixtures typically have a broader spectrum of activity than the compound of general formula I alone. Furthermore, the other components can be selected so as to exert a synergistic effect on the pesticidal activity of the compound of general formula I.

Combinations of at least two herbicides can be included in a single formulation or later added in a suitable form during the preparation of the tank mix. Exemplary herbicides which can be used in such mixtures include the following:

amethydione, bilanafos, metabenzthiazuron, metamitron, metribuzin, 2,4-D, 2,4-DB, 2,4-DP, alachlor, alloxydim, asulam, atrazine, bensulfuron, bentazon, bifenox, bromoxynil, butachlor, carfentratone, chloridazon, chlorimuron, chlorpropham, chlorsulfuron, chlortoluron, cinmethylin, clopyralid, cyanazine, cycloate, cyclosulfamuron, cycloxydim, dichlobenil, diclofop, dimethenamid, EPTC, ethiozin, fenoxaprop, flamprop, fluazifop, fluometuron, fluridone, fluroxypyr, fomesafen, glufosinate, glyphosate, haloxyfop, hexazinone, imazamethabenz, imazamethapyr, imazamox, imazapyr, imazaquin, imazethapyr, ioxynil, isoproturon, isoxaflutole, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofop, sethoxydim, simetryn, terbutryn, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, sulfentrazone, thiameturon, thifensulfuron, triasulfuron, tribenuron, esprocarb, prosulfocarb, terbutylazin, benfuresate, clomazone, dimethazone, dithiopyr, isoxaben, quinchlorac, quinmerac, sulfosate.

Mixtures with other active ingredients like fungicides, insecticides, acaricides and nematicides are also possible.

A formulation containing a compound according to the invention can consist of 100 g of active ingredient (compound of formula I), 30 g of disperging agent, 3 g of antifoaming agent, 2 g of structure agent, 50 g of antifreezing agent, 0.5 g of a biocidal agent and water ad 1000 ml. Prior to use it is diluted with water to give the desired concentration of active ingredient.

For a clearer understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR (nuclear magnetic resources and MS (mass spectrometry).

EXAMPLE 1

Preparation of 2-(5-trifluoromethyl-[1,3,4]-thiadiazol-2-yloxy)-N-ethyl-N-3,3,5-trimethyl-cyclohexa-1,5-dienyl)-acetamide 1A Ethyl-(3,5,5-trimethyl-cyclohex-2-enylidene)-amine Ethylamine (42 ml of a 70% solution in water, 530 mmol) is added slowly to a stirred mixture of isophorone (9.67 g, 70 mmol) and ethylamine hydrochloride (0.29 g, 3.5 mmol) at -7° C. After the addition is complete, the temperature of the mixture is allowed to rise to room temperature, and the mixture is stirred for a further 72 hours. The mixture is subsequently cooled to 10° C., and potassium hydroxide (44.9 g, 800 mmol) is added in portions. After 45 minutes, ice is added and the mixture is stirred. The organic phase is then separated, dried over sodium sulfate and evaporated in vacuo to give the crude product (11.0 g, 95%) as a yellow oil, which is used immediately without further purification in the following step.

1B 2-Acetoxy-N-ethyl-N-(3,3,5-trimethyl-cyclohexa-1,5-dienyl)-acetamide

2-Acetoxyacetyl chloride (6.42 g, 4.7 mmol) is added slowly to a mixture of 1A (7.62 g, 4.2 mmol) and toluene (50 ml), which is cooled to −5° C. After the addition is complete, the mixture is stirred for a further 1 hour at −5° C., then allowed to warm to room temperature and stirred for a further 1.5 hours. The reaction mixture is then cooled down to −3° C. and a mixture of triethylamine (6.5 ml, 4.7 mmol) and toluene (25 ml) is added slowly to the mixture. The mixture is stirred for a further 16 hours, during which time the temperature is gradually allowed to rise to room temperature. The mixture is filtered, and the filtrate is washed three times with water, dried over sodium sulfate and evaporated in vacuo to give the crude product (12.0 g, 89%) as an oil. A portion of this crude material (4 g) is purified by flash column chromatography, eluting with a mixture of ethyl acetate and petroleum ether (1:4) to give pure product (2.3 g, equivalent to 51% overall), with m.p. 38–40° C. NMR analysis of this indicates that the product has a purity of about 88 mol %, the impurity consisting mainly of two isomeric products.

1C 2-Hydroxy-N-ethyl-N-(3,3,5-trimethyl-cyclohexa-1,5-dienyl)-acetamide

A mixture of potassium hydroxide (0.47 g, 8.3 mmol) and water (5 ml) is added to 1B (2.2 g, 8.3 mmol) in ethanol (10 ml) and the mixture is stirred for 3 hours at room temperature. The solvent is evaporated in vacuo and the resulting residue is dissolved in dichloromethane. The organic solution is washed twice with a small quantity of water, dried over sodium sulfate and evaporated in vacuo to give the product (1.6 g, 86%) as beige crystals, m.p. 53–56° C. NMR analysis indicates that the product has a purity of 84 mol %, the major contaminant being the other diene isomer.

1D 2-(5-Trifluoromethyl-[1,3,4]-thiadiazol-2-yloxy)-N-ethyl-N-3,3,5-trimethyl-cyclohexa-1,5-dienyl)-acetamide Sodium hydride (0.15 g of a 60% suspension in oil, 3.8 mmol) is added to a stirred mixture of 1C (0.78 g, 3.5 mmol) and THF (tetrahydrofuran)(10 ml) and the mixture is stirred for 30 minutes. A mixture of 2-methanesulfonyl-5-trifluoromethyl-[1,3,4]-thiadiazole (0.81 g, 3.5 mmol) and THF (5 ml) is then added to the stirred suspension, and the mixture is stirred for a further 16 hours at room temperature. The solvent is removed by evaporation in vacuo, and the resulting oil is purified by flash column chromatography, eluting with a mixture of ethyl acetate and petroleum ether (1:4) to give the product (0.45 g, 34%) as a yellow oil. NMR analysis confirms that the structure of the product is correct.

EXAMPLE 2

Preparation of 2-(benzoxazol-2-yloxy)-N-ethyl-N-3,3,5-trimethyl-cyclohexa-1,5-dienyl)-acetamide Sodium hydride (0.15 g of a 60% suspension in oil, 3.8 mmol) is added to a stirred mixture of 1C (0.78 g, 3.5 mmol) and THF (10 ml) and the mixture is stirred for 30 minutes. A mixture of 2-chlorobenzoxazole (0.54 g, 3.5 mmol) and THF (5 ml) is then added to the stirred suspension, and the mixture is stirred for a further 16 hours at room temperature. The solvent is removed by evaporation in vacuo, and the solid residue is recrystallized from diisopropyl ether to give the product (0.58 g, 49%) as beige crystals, m.p. 97–99° C. NMR analysis confirms that the structure of the product is correct.

EXAMPLE 3–15

Further compounds of the invention are prepared according to the general method of Examples 1 and 2 and are listed in Tables 1 and 2 (for the sake of simplicity the tables show only the major product which contain the 3,3,5-trimethylcyclohexa-1,3-dienyl moiety).

TABLE 1

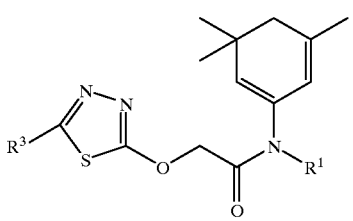

| Example No. | $R^1$ | $R^3$ | |
|---|---|---|---|
| 3 | methyl | trifluoromethyl | mp. 54–57° C. |
| 4 | isopropyl | trifluoromethyl | oil |

TABLE 1-continued

[Structure: R³-substituted thiadiazole-O-CH₂-C(=O)-N(R¹)-(3,5-dimethylphenyl)]

| Example No. | R¹ | R³ | |
|---|---|---|---|
| 5 | methyl | ethyl | oil |
| 6 | ethyl | ethyl | oil |
| 7 | methyl | pentafluoroethyl | oil |
| 8 | ethyl | pentafluoroethyl | mp. 55° C. |
| 9 | methyl | tert-butyl | oil |
| 10 | ethyl | tert-butyl | |
| 11 | isopropyl | ethyl | oil |
| 12 | isopropyl | pentafluoroethyl | |
| 13 | isopropyl | tert-butyl | |
| 14 | 2-methoxyethyl | trifluoromethyl | |
| 15 | cyclopropyl | trifluoromethyl | |

EXAMPLE 16–34

Further Examples are prepared according to the general method of Examples 1 and 2 and are listed in Table 2.

TABLE 2

[Structure: Y-substituted benzo-fused X-heterocycle-O-CH₂-C(=O)-N(R¹)-(3,5-di-tert-substituted phenyl with H₃C groups)]

| Example No. | Y | X | R¹ | |
|---|---|---|---|---|
| 16 | H | O | methyl | mp. 77–81° C. |
| 17 | H | O | i-propyl | oil |
| 18 | H | O | 2-methoxyethyl | |
| 19 | 5-Cl | O | methyl | |
| 20 | 5-Cl | O | ethyl | |
| 21 | 5-Cl | O | isopropyl | |
| 22 | 6-Cl | O | methyl | |
| 23 | 6-Cl | O | ethyl | |
| 24 | 6-Cl | O | isopropyl | |
| 25 | 5-Cl | O | 2-methoxyethyl | |
| 26 | 6-Cl | O | 2-methoxyethyl | |
| 27 | 5-methyl | O | methyl | |
| 28 | 5-methyl | O | ethyl | |
| 29 | 5-methyl | O | isopropyl | |
| 30 | 5-methyl | O | 2-methoxyethyl | |
| 31 | H | S | methyl | |
| 32 | H | S | ethyl | |
| 33 | H | S | isopropyl | |
| 34 | H | S | 2-methoxyethyl | |

EXAMPLE 35–43

Further Examples are prepared according to the general method of Examples 1 and 2 and are listed in Table 3.

TABLE 3

[Structure: Het-O-CH₂-C(=O)-N(R¹)-(3,5-dimethylphenyl)]

| Example No. | Het | R¹ |
|---|---|---|
| 35 | 5-methyl-1-phenyl-1H-tetrazol-yl | i-propyl |
| 36 | 5-methyl-1-phenyl-1H-tetrazol-yl | ethyl |
| 37 | 5-methyl-1-phenyl-1H-tetrazol-yl | methyl |
| 38 | 3-CF₃-5-methyl-1,2,4-thiadiazolyl | ethyl |
| 39 | 3-CF₃-5-methyl-1,2,4-oxadiazolyl | ethyl |
| 40 | 3-CF₃-4-Cl-5-methyl-1-phenylpyrazolyl | i-propyl |

TABLE 3-continued

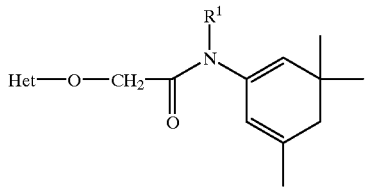

| Example No. | Het | R[1] |
|---|---|---|
| 41 | 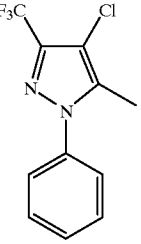 | ethyl |
| 42 | | methyl |
| 43 | 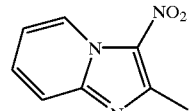 | ethyl |

Herbicidal Activity

The compounds of the invention are tested for pre- and post-emergence herbicidal activity. The species included in the test are set forth below.

| | Plant Species Used | |
|---|---|---|
| TRZAW | *Triticum aestivum* | winter wheat |
| HORVW | *Hordeum vulgare* | winter barley |
| ZEAMX | *Zea mays* | maize |
| GLXMX | *Glycine max* | soybeans |
| ORYSA | *Oryza sativum* | rice |
| AMATA | *Amaranthus tuberculatus* | waterhemp |
| GALAP | *Galium aparine* | cleavers |
| ALOMY | *Alopecurus myosuroides* | blackgrass |
| APESV | *Apera spica venti* | bentgrass |
| ECHCG | *Echinochloa crus-galli* | barnyardgrass |
| SETVI | *Setaria viridis* | green foxtail |
| LOLPE | *Lolium perenne* | eavers |

Each pot is examined three weeks after treatment and phytotoxicity is assessed according to the rating system set forth below.

| Rating System | % Difference in Growth Versus Untreated Control |
|---|---|
| 0 - No effect | 0 |
| 1 - Trace effect | 1–5 |
| 2 - Slight effect | 6–15 |
| 3 - Moderate effect | 16–29 |
| 4 - Injury | 30–44 |
| 5 - Definite injury | 45–64 |
| 6 - Herbicidal effect | 65–79 |
| 7 - Good herbicidal effect | 80–90 |
| 8 - Approaching complete kill | 91–99 |
| 9 - Complete kill | 100 |

PRE-emergence Herbicidal Evaluation of Test Compounds

The pre-emergence herbicidal activity of the compounds of the present invention is exemplified by the following test in which the seeds of a variety of monocotyledonous and dicotyledonous plants are seperately mixed with potting soil and planted on top of approximately one inch of soil in separate pots. After planting, the pots are sprayed with the selected aqueous acetone solution containing test compound in sufficient quantity to provide the equivalent of about 0.8 to 0.1 kg per hectare of test compound per pot. The treated pots are then placed on greenhouse benches, watered and cared for in accordance with conventional greenhouse procedures. The results are set out in Table 4 below.

TABLE 4

PRE-EMERGENCE APPLICATION:

| Compound of Example | Rate [kg/ha] | AMATA | GALAP | ALOMY | APESV | ECHCG | SETVI | LOLPE | TRZAW | HORVW | ZEAMX | GLXMA | ORYSA |
|---|---|---|---|---|---|---|---|---|---|---|---|---|---|
| 1 | 0.800 | 9 | 4 | 7 | 9 | 9 | 8 | 9 | 4 | 4 | 4 | 2 | X |
| | 0.400 | 9 | 4 | 9 | 9 | 9 | 8 | 9 | 2 | 4 | 2 | 2 | 3 |
| | 0.200 | 3 | 4 | 3 | 8 | 8 | 7 | 3 | 0 | 2 | 0 | 0 | 0 |
| | 0.100 | 0 | 0 | 2 | 6 | 4 | 4 | 2 | 0 | 2 | 0 | 0 | 0 |
| 2 | 0.800 | 8 | 0 | 6 | 9 | 9 | 8 | 9 | 2 | 3 | 1 | 0 | 2 |
| | 0.400 | 8 | 0 | 6 | 9 | 8 | 7 | 8 | 2 | 2 | 0 | 0 | 0 |
| | 0.200 | 6 | 0 | 5 | 6 | 5 | 4 | 2 | 0 | 2 | 0 | 0 | 0 |
| | 0.100 | 2 | 0 | 1 | 1 | 3 | 1 | 0 | 0 | 0 | 0 | 0 | 0 |
| 3 | 0.800 | 8 | X | 9 | 9 | 9 | 9 | 9 | 3 | 4 | 7 | 0 | 6 |
| | 0.400 | 6 | X | 8 | 8 | 8 | 8 | 9 | 1 | 1 | 3 | 0 | 6 |
| | 0.200 | 0 | X | 8 | 6 | 8 | 8 | 7 | 1 | 1 | 1 | 0 | 3 |
| | 0.100 | 0 | X | 6 | 3 | 6 | 6 | 3 | 0 | 0 | 0 | 0 | 1 |
| 4 | 0.800 | 8 | 3 | 9 | 9 | 9 | 9 | 9 | 4 | 4 | 4 | 1 | 5 |
| | 0.400 | 8 | 2 | 7 | 9 | 9 | 6 | 9 | 1 | 1 | 1 | 0 | 5 |

TABLE 4-continued

PRE-EMERGENCE APPLICATION:

| Compound of Example | Rate [kg/ha] | AMATA | GALAP | ALOMY | APESV | ECHCG | SETVI | LOLPE | TRZAW | HORVW | ZEAMX | GLXMA | ORYSA |
|---|---|---|---|---|---|---|---|---|---|---|---|---|---|
|   | 0.200 | 6 | 0 | 7 | 9 | 9 | 6 | 9 | 0 | 0 | 1 | 0 | 4 |
|   | 0.100 | 6 | 0 | 7 | 9 | 6 | 6 | 8 | 0 | 0 | 0 | 0 | 3 |
| 5 | 0.800 | 3 | X | 9 | 7 | 9 | 9 | 7 | 1 | 4 | 6 | 1 | 5 |
|   | 0.400 | 1 | X | 9 | 3 | 8 | 7 | 5 | 1 | 3 | 0 | 0 | 4 |
|   | 0.200 | 0 | X | 8 | X | 7 | 3 | 5 | 0 | 2 | 0 | 0 | 2 |
|   | 0.100 | 0 | X | 3 | X | 2 | 0 | 5 | 0 | 0 | 0 | 0 | 1 |
| 6 | 0.800 | 5 | X | 9 | 9 | 9 | 9 | 7 | 2 | 3 | 0 | 0 | 7 |
|   | 0.400 | 0 | X | 6 | 0 | 8 | 8 | 5 | 0 | 1 | 0 | 0 | 3 |
|   | 0.200 | 0 | X | 5 | 0 | 6 | 5 | 0 | 0 | 0 | 0 | 0 | 0 |
|   | 0.100 | 0 | X | i | 0 | 3 | i | 0 | 0 | 0 | 0 | 0 | 0 |
| 7 | 0.800 | 3 | X | 5 | 7 | 9 | 2 | 9 | 0 | 1 | 1 | 0 | 2 |
|   | 0.400 | 3 | X | 5 | 0 | 6 | 0 | 3 | 0 | 1 | 0 | 0 | 0 |
|   | 0.200 | 0 | X | 2 | 0 | 0 | 0 | 0 | 0 | 0 | 0 | 0 | 0 |
|   | 0.100 | 0 | X | 0 | X | 0 | 0 | 0 | 0 | 0 | 0 | 0 | 0 |
| 8 | 0.800 | 6 | X | 8 | 9 | 8 | 7 | 6 | 0 | 2 | 0 | 0 | 1 |
|   | 0.400 | 5 | X | 6 | 8 | 4 | 4 | 6 | 0 | 1 | 0 | 0 | 0 |
|   | 0.200 | 1 | X | 4 | 0 | 4 | 4 | 4 | 0 | 0 | 0 | 0 | 0 |
|   | 0.100 | 0 | X | 1 | 0 | 1 | 1 | 1 | 0 | 0 | 0 | 0 | 0 |
| 11 | 0.800 | 4 | X | 9 | 5 | 9 | 9 | 9 | 3 | 4 | 7 | 0 | 6 |
|   | 0.400 | 0 | X | 8 | 5 | 9 | 8 | 8 | 2 | 1 | 0 | 0 | 4 |
|   | 0.200 | 0 | X | 8 | 0 | 7 | 8 | 5 | 0 | 0 | 0 | 0 | 1 |
|   | 0.100 | 0 | X | 7 | 0 | 7 | 6 | 4 | 0 | 0 | 0 | 0 | 0 |
| 16 | 0.800 | 7 | X | 9 | 9 | 9 | 9 | 8 | 1 | 3 | 0 | 0 | 5 |
|   | 0.400 | 3 | X | 8 | 8 | 7 | 9 | 3 | 0 | 2 | 0 | 0 | 2 |
|   | 0.200 | 3 | X | 8 | 4 | 6 | 8 | 0 | 0 | 0 | 0 | 0 | 0 |
|   | 0.100 | 0 | X | 6 | X | 5 | 5 | 0 | 0 | 0 | 0 | 0 | 0 |
| 17 | 0.800 | 9 | 0 | 9 | 9 | 9 | 8 | 9 | 4 | 4 | 3 | 1 | 4 |
|   | 0.400 | 5 | 0 | 6 | 9 | 7 | 8 | 9 | 2 | 2 | 1 | 0 | 4 |
|   | 0.200 | 5 | 0 | 6 | 8 | 6 | 5 | 9 | 2 | 2 | 0 | 0 | 3 |
|   | 0.100 | 4 | 0 | 3 | 7 | 4 | 3 | 5 | 1 | 1 | 0 | 0 | 2 |

Post-emergence Herbicidal Evaluation of Test Compounds

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels equivalent of about 0.4 to 0.1 kg per hectare of test compound per pot. After spraying the plants are placed on greenhouse benches and are cared for in the usual manner, commensurate with conventional greenhouse practices. The results of the test are set out in Table 5 below.

TABLE 5

POST-EMERGENCE APPLICATION

| Example | [kg/ha] | AMATA | GALAP | ALOMY | APESV | ECHCG | SETVI | LOLPE | TRZAW | HORVW | ZEAMX | GLXMA | ORYSA |
|---|---|---|---|---|---|---|---|---|---|---|---|---|---|
| 1 | 0.400 | 0 | 1 | 8 | 8 | 7 | 3 | 8 | 1 | 0 | 0 | 4 | 3 |
|   | 0.200 | 0 | 0 | 6 | 8 | 4 | 2 | 8 | 0 | 0 | 0 | 5 | 0 |
|   | 0.100 | 0 | 0 | 6 | 5 | 2 | 0 | 6 | 0 | 0 | 0 | 4 | 0 |
| 2 | 0.400 | 6 | 3 | 7 | 7 | 8 | 6 | 8 | 1 | 2 | 0 | 7 | 1 |
|   | 0.200 | 6 | 2 | 4 | 7 | 2 | 2 | 7 | 0 | 2 | 0 | 7 | 0 |
|   | 0.100 | 5 | 0 | 0 | 6 | 1 | 0 | 5 | 0 | 1 | 0 | 5 | 0 |
| 3 | 0.400 | 0 | 5 | 7 | 3 | 4 | 0 | 7 | 3 | 2 | 0 | 4 | 2 |
|   | 0.200 | 0 | 4 | 4 | 6 | 1 | 0 | 7 | 1 | 0 | 0 | 2 | 0 |
| 4 | 0.400 | 4 | 2 | 8 | 8 | 6 | 5 | 8 | 3 | 2 | 0 | 6 | 1 |
|   | 0.200 | 1 | 0 | 8 | 8 | 6 | 5 | 7 | 1 | 1 | 0 | 4 | 1 |
|   | 0.100 | 1 | 0 | 4 | 2 | 3 | 3 | 5 | 0 | 0 | 0 | 2 | 0 |
| 5 | 0.400 | 3 | 4 | 7 | 1 | 0 | 0 | 4 | 1 | 0 | 0 | 5 | 1 |
|   | 0.200 | 0 | 0 | 2 | 0 | 0 | 0 | 1 | 0 | 0 | 0 | 5 | 1 |
|   | 0.100 | 0 | 0 | 0 | 0 | 0 | 0 | 0 | 0 | 0 | 0 | 5 | 0 |
| 6 | 0.400 | 0 | 4 | 8 | 1 | 0 | 0 | 0 | 1 | 0 | 0 | 4 | 2 |
|   | 0.200 | 0 | 0 | 4 | 0 | 0 | 0 | 0 | 0 | 0 | 0 | 4 | 1 |
|   | 0.100 | 0 | 0 | 0 | 0 | 0 | 0 | 0 | 0 | 0 | 0 | 3 | 0 |
| 7 | 0.400 | 5 | 5 | 4 | 2 | 0 | 0 | 6 | 0 | 0 | 0 | 5 | 3 |
|   | 0.200 | 3 | 3 | 0 | 0 | 0 | 0 | 6 | 0 | 0 | 0 | 2 | 0 |
|   | 0.100 | 3 | 0 | 0 | 0 | 0 | 0 | 0 | 0 | 0 | 0 | 2 | 0 |

TABLE 5-continued

| | | POST-EMERGENCE APPLICATION | | | | | | | | | | |
|---|---|---|---|---|---|---|---|---|---|---|---|---|
| Example | [kg/ha] | AMATA | GALAP | ALOMY | APESV | ECHCG | SETVI | LOLPE | TRZAW | HORVW | ZEAMX | GLXMA | ORYSA |
| 8 | 0.400 | 0 | 5 | 4 | 6 | 0 | 0 | 8 | 1 | 0 | 0 | 4 | 2 |
| | 0.200 | 0 | 0 | 4 | 4 | 0 | 0 | 7 | 0 | 0 | 0 | 3 | 0 |
| | 0.100 | 0 | 0 | 0 | 0 | 0 | 0 | 1 | 0 | 0 | 0 | 2 | 0 |
| 11 | 0.400 | 4 | 0 | 8 | 5 | 3 | 0 | 8 | 1 | 1 | 4 | 5 | 2 |
| | 0.200 | 3 | 0 | 7 | 7 | 2 | 0 | 5 | 0 | 0 | 1 | 5 | 0 |
| | 0.100 | 0 | 0 | 1 | 0 | 0 | 0 | 3 | 0 | 0 | 0 | 3 | 0 |
| 16 | 0.400 | 3 | 4 | 7 | 4 | 0 | 0 | 7 | 0 | 2 | 0 | 4 | 2 |
| | 0.200 | X | 3 | 5 | 6 | 0 | 0 | 6 | 0 | 0 | 0 | 3 | 0 |
| | 0.100 | 3 | 3 | 2 | 0 | 0 | 0 | 4 | 0 | 0 | 0 | 2 | 0 |
| 17 | 0.400 | 5 | 4 | 8 | 8 | 6 | 6 | 8 | 2 | 0 | 1 | 6 | 4 |
| | 0.200 | 4 | 3 | 6 | 8 | 4 | 6 | 7 | 1 | 0 | 0 | 3 | 3 |
| | 0.100 | 3 | 1 | 3 | 6 | 3 | 5 | 4 | 0 | 0 | 0 | 3 | 0 |

What is claimed is:

1. A compound of the general formula (I)

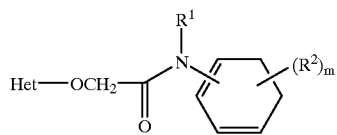

(I)

wherein

Het represents an optionally substituted, optionally benzofused nitrogen containing 5- or 6-membered heteroaromatic group;

$R^1$ represents an alkyl, alkoxyalkyl or cycloalkyl group;

$R^2$ each independently represent an alkyl or alkenyl group, and m represents 0 or an integer from 1 to 6.

2. A compound according to claim 1 wherein $R^2$ each independently represent a $C_{1-4}$ alkyl or group $C_{2-4}$ alkenyl and m is 1, 2 or 3.

3. A compound according to claim 1 wherein Het represents a thiadiazolyl, benzoxazolyl or benzothiazolyl group which may be substituted by one or more halogen atoms or alkyl, haloalkyl, haloalkoxy or phenyl groups.

4. A compound according to claim 3 wherein Het represents a group selected from the formulae (1) and (2)

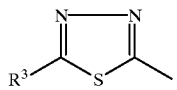

(1)

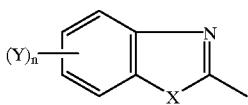

(2)

in which $R^3$ represents a hydrogen or halogen atom or an alkyl or haloalkyl group;

X represents O or S;

Y represents independently of each other a halogen atom or an optionally substituted alkyl group; and n is an integer from 0 to 4.

5. A compound according to claim 1 wherein $R^2$ represents a methyl group and m is 3.

6. A compound as claimed in claim 1, wherein $R^1$ represents a $C_{1-5}$ alkyl, a cyclopropyl or a 2-methoxyethyl group.

7. A compound of formula IA,

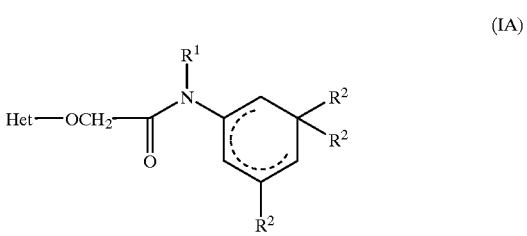

(IA)

wherein Het, $R^1$ and $R^2$ are as defined in claim 1 and the dashed line indicates the presence of two conjugated double bonds in one or the other position with respect to the point of attachment of the nitrogen atom.

8. A compound according to claim 7 selected from the formulae IA1 and IA2,

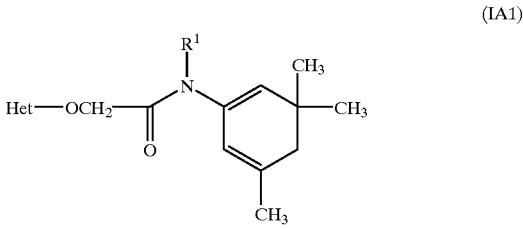

(IA1)

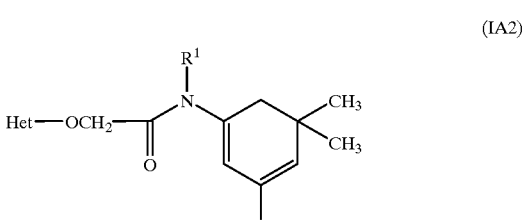

(IA2)

wherein $R^1$ represents an alkyl or alkoxyalkyl group,

Het represents a group selected from the formulae (1) and (2)

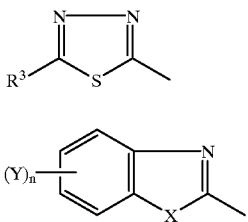

(1)

(2)

in which X has the meaning given, and
Y represents a halogen atom or a methyl group,
n is 0 or 1, and
$R^3$ represents a $C_{1-4}$ alkyl or $C_{1-4}$ fluoroalkyl group.

9. An isomeric mixture of the two compounds of formula IA of claim 7 which differ only in the location of the conjugated double bonds.

10. The compounds according to claim 1 selected from the group consisting of
2-(5-trifluoromethyl-[1,3,4]-thiadiazol-2-yloxy)-N-methyl-N-(3,5,5-trimethylcyclohexa-1,3-dienyl)-acetamide,
2-(5-trifluoromethyl-[1,3,4]-thiadiazol-2-yloxy)-N-ethyl-N-(3,5,5-trimethylcyclohexa-1,3-dienyl)-acetamide,
2-(5-trifluoromethyl-[1,3,4]-thiadiazol-2-yloxy)-N-methyl-N-(3,3,5-trimethylcyclohexa-1,5-dienyl)-acetamide,
2-(5-trifluoromethyl-[1,3,4]-thiadiazol-2-yloxy)-N-ethyl-N-(3,3,5-trimethylcyclohexa-1,5-dienyl)-acetamide,
2-(5-ethyl-[1,3,4]-thiadiazol-2-yloxy)-N-methyl-N-(3,5,5-trimethylcyclohexa-1,3-dienyl)-acetamide,
2-(5-ethyl-[1,3,4]-thiadiazol-2-yloxy)-N-ethyl-N-(3,5,5-trimethylcyclohexa-1,3-dienyl)-acetamide,
2-(5-ethyl-[1,3,4]-thiadiazol-2-yloxy)-N-methyl-N-(3,3,5-trimethylcyclohexa-1,5-dienyl)-acetamide,
2-(5-ethyl-[1,3,4]-thiadiazol-2-yloxy)-N-ethyl-N-(3,3,5-trimethylcyclohexa-1,5-dienyl)-acetamide,
2-(5-pentafluoroethyl-[1,3,4]-thiadiazol-2-yloxy)-N-methyl-N-(3,5,5-trimethylcyclohexa-1,3-dienyl)-acetamide,
2-(5-pentafluoroethyl-[1,3,4]-thiadiazol-2-yloxy)-N-ethyl-N-(3,5,5-trimethylcyclohexa-1,3-dienyl)-acetamide,
2-(5-pentafluoroethyl-[1,3,4]-thiadiazol-2-yloxy)-N-methyl-N-(3,3,5-trimethylcyclohexa-1,5-dienyl)-acetamide,
2-(5-pentafluoroethyl-[1,3,4]-thiadiazol-2-yloxy)-N-ethyl-N-(3,3,5-trimethylcyclohexa-1,5-dienyl)-acetamide,
2-(5- tert-butyl-[1,3,4]-thiadiazol-2-yloxy)-N-methyl-N-(3,5,5-trimethylcyclohexa-1,3-dienyl)-acetamide,
2-(5- tert-butyl-[1,3,4]-thiadiazol-2-yloxy)-N-ethyl-N-(3,5,5-trimethylcyclohexa-1,3-dienyl)-acetamide,
2-(5- tert-butyl-[1,3,4]-thiadiazol-2-yloxy)-N-methyl-N-(3,3,5-trimethylcyclohexa-1,5-dienyl)-acetamide,
2-(5- tert-butyl-[1,3,4]-thiadiazol-2-yloxy)-N-ethyl-N-(3,3,5-trimethylcyclohexa-1,5-dienyl)-acetamide,
2-(5-trifluoromethyl-[1,3,4]-thiadiazol-2-yloxy)-N-isopropyl-N-(3,5,5-trimethylcyclohexa-1,3-dienyl)-acetamide,
2-(5-trifluoromethyl-[1,3,4]-thiadiazol-2-yloxy)-N-isopropyl-N-(3,3,5-trimethylcyclohexa-1,5-dienyl)-acetamide,
2-(5-ethyl-[1,3,4]-thiadiazol-2-yloxy)-N-isopropyl-N-(3,5,5-trimethylcyclohexa-1,3-dienyl)-acetamide,
2-(5-ethyl-[1,3,4]-thiadiazol-2-yloxy)-N-isopropyl-N-(3,3,5-trimethylcyclohexa-1,5-dienyl)-acetamide,
2-(5-pentafluoroethyl-[1,3,4]-thiadiazol-2-yloxy)-N-isopropyl-N-(3,5,5-trimethylcyclohexa-1,3-dienyl)-acetamide,
2-(5-pentafluoroethyl-[1,3,4]-thiadiazol-2-yloxy)-N-isopropyl-N-(3,3,5-trimethylcyclohexa-1,5-dienyl)-acetamide,
2-(5-tert-butyl-[1,3,4]-thiadiazol-2-yloxy)-N-isopropyl-N-(3,5,5-trimethylcyclohexa-1,3-dienyl)-acetamide,
2-(5-tert-butyl-[1,3,4]-thiadiazol-2-yloxy)-N-isopropyl-N-(3,3,5-2-(5-trifluoromethyl-[1,3,4]-thiadiazol-2-yloxy)-N-(2-methoxyethyl)-N-(3,5,5-trimethylcyclohexa-1,3-dienyl)-acetamide,
2-(5-trifluoromethyl-[1,3,4]-thiadiazol-2-yloxy)-N-(2-methoxyethyl)-N-(3,3,5-trimethylcyclohexa-1,5-dienyl)-acetamide,
2-(5-trifluoromethyl-[1,3,4]-thiadiazol-2-yloxy)-N-cyclopropyl-N-(3,5,5-trimethylcyclohexa-1,3-dienyl)-acetamide,
2-(5-trifluoromethyl-[1,3,4]-thiadiazol-2-yloxy)-N-cyclopropyl-N-(3,3,5-trimethylcyclohexa-1,5-dienyl)-acetamide,
2-(benzoxazol-2-yloxy)-N-methyl-N-(3,5,5-trimethylcyclohexa-1,3-dienyl)-acetamide,
2-(benzoxazol-2-yloxy)-N-methyl-N-(3,3,5-trimethylcyclohexa-1,5-dienyl)-acetamide,
2-(benzoxazol-2-yloxy)-N-ethyl-N-(3,5,5-trimethylcyclohexa-1,3-dienyl)-acetamide,
2-(benzoxazol-2-yloxy)-N-ethyl- N-(3,3,5-trimethylcyclohexa-1,5-dienyl)-acetamide,
2-(benzoxazol-2-yloxy)-N-isopropyl-N-(3,5,5-trimethylcyclohexa-1,3-dienyl)-acetamide,
2-(benzoxazol-2-yloxy)-N-isopropyl-N-(3,3,5-trimethylcyclohexa-1,5-dienyl)-acetamide,
2-(benzoxazol -2-yloxy)-N-(2-methoxyethyl)-N-(3,5,5-trimethylcyclohexa-1,3-dienyl)-acetamide,
2-(benzoxazol-2-yloxy)-N-(2-methoxyethyl)-N-(3,3,5-trimethylcyclohexa-1,5-dienyl)-acetamide,
2-(5-chloro-benzoxazol-2-yloxy)-N-methyl-N-(3,5,5-trimethylcyclohexa-1,3-dienyl)-acetamide,
2-(5-chloro-benzoxazol-2-yloxy)-N-methyl-N-(3,3,5-trimethylcyclohexa-1,5-dienyl)-acetamide,
2-(5-chloro-benzoxazol-2-yloxy)-N-ethyl-N-(3,5,5-trimethylcyclohexa-1,3-dienyl)-acetamide,
2-(5-chloro-benzoxazol-2-yloxy)-N-ethyl-N-(3,3,5-trimethylcyclohexa-1,5-dienyl)-acetamide,
2-(5-chloro-benzoxazol-2-yloxy)-N-isopropyl-N-(3,5,5-trimethylcyclohexa-1,3-dienyl)-acetamide,
2-(5-chloro-benzoxazol-2-yloxy)-N-isopropyl-N-(3,3,5-trimethylcyclohexa-1,5-dienyl)-acetamide,
2-(6-chloro-benzoxazol-2-yloxy)-N-methyl-N-(3,5,5-trimethylcyclohexa-1,3-dienyl)-acetamide,
2-(6-chloro-benzoxazol-2-yloxy)-N-methyl-N-(3,3,5-trimethylcyclohexa-1,5-dienyl)-acetamide,
2-(6-chloro-benzoxazol-2-yloxy)-N-ethyl-N-(3,5,5-trimethylcyclohexa-1,3-dienyl)-acetamide,
2-(6-chloro-benzoxazol-2-yloxy)-N-ethyl-N-(3,3,5-trimethylcyclohexa-1,5-dienyl)-acetamide,
2-(benzoxazol-2-yloxy)-N-isopropyl-N-(3,5,5-trimethylcyclohexa-1,3-dienyl)-acetamide,
2-(6-chloro-benzoxazol-2-yloxy)-N-isopropyl-N-(3,5,5-trimethylcyclohexa-1,3-dienyl)-acetamide,
2-(5-chloro-benzoxazol-2-yloxy)-N-(2-methoxyethyl)-N-(3,5,5-trimethylcyclohexa-1,3-dienyl)-acetamide,
2-(5-chloro-benzoxazol-2-yloxy)-N-(2-methoxyethyl)-N-(3,3,5-trimethylcyclohexa-1,5-dienyl)-acetamide,
2-(6-chloro-benzoxazol-2-yloxy)-N-(2-methoxyethyl)-N-(3,5,5-trimethylcyclohexa-1,3-dienyl)-acetamide,
2-(6-chloro-benzoxazol-2-yloxy)-N-(2-methoxyethyl)-N-(3,3,5-trimethylcyclohexa-1,5-dienyl)-acetamide,
2-(5-methyl-benzoxazol-2-yloxy)-N-methyl-N-(3,5,5-trimethylcyclohexa-1,3-dienyl)-acetamide, 2-(5-methyl-benzoxazol-2-yloxy)-N-methyl-N-(3,3,5-trimethylcyclohexa-1,5-dienyl)-acetamide,
2-(5-methyl-benzoxazol-2-yloxy)-N-ethyl-N-(3,5,5-trimethylcyclohexa-1,3-dienyl)-acetamide,
2-(5-methyl-benzoxazol-2-yloxy)-N-ethyl-N-(3,3,5-trimethylcyclohexa-1,5-dienyl)-acetamide,
2-(5-methyl-benzoxazol-2-yloxy)-N-isopropyl-N-(3,5,5-trimethylcyclohexa-1,3-dienyl)-acetamide,
2-(5-methyl-benzoxazol-2-yloxy)-N-isopropyl-N-(3,3,5-trimethylcyclohexa-1,5-dienyl)-acetamide,
2-(5-methyl-benzoxazol-2-yloxy)-N-(2-methoxyethyl)-N-(3,5,5-trimethylcyclohexa-1,3-dienyl)-acetamide,
2-(5-methyl-benzoxazol-2-yloxy)-N-(2-methoxyethyl)-N-(3,3,5-trimethylcyclohexa-1,5-dienyl)-acetamide,
2-(benzothiazol-2-yloxy)-N-methyl-N-(3,5,5-trimethylcyclohexa-1,3-dienyl)-acetamide,
2-(benzothiazol-2-yloxy)-N-methyl-N-(3,3,5-trimethylcyclohexa-1,5-enyl)-acetamide,
2-(benzothiazol-2-yloxy)-N-ethyl-N-(3,5,5-trimethylcyclohexa-1,3-dienyl)-acetamide,
2-(benzothiazol-2-yloxy)-N-ethyl-N-(3,3,5-trimethylcyclohexa-1,5-enyl)-acetamide,
2-(benzothiazol-2-yloxy)-N-isopropyl-N-(3,5,5-trimethylcyclohexa-1,3-dienyl)-acetamide,
2-(benzothiazol-2-yloxy)-N-isopropyl-N-(3,3,5-trimethylcyclohexa-1,5-dienyl)-acetamide,
2-(benzothiazol-2-yloxy)-N-(2-methoxyethyl)-N-(3,5,5-trimethylcyclohexa-1,3-dienyl)-acetamide,
2-(benzothiazol-2-yloxy)-N-(2-methoxyethyl)-N-(3,3,5-trimethylcyclohexa-1,5-dienyl)-acetamide.

11. A process for the preparation of a compound according to claim 1 which comprises reacting a compound of the general formula II,

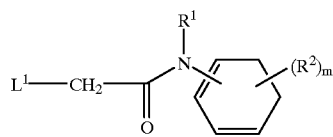

(II)

in which $R^1$, $R^2$ and m are defined in claim 1 with a compound of general formula III,

(III)

wherein Het represents an alkyl, alkoxyalkyl, or cycloalkyl group and one of $L^1$ and $L^2$ represents a hydroxy group and the other represents a leaving group.

12. A compound of the general formula II,

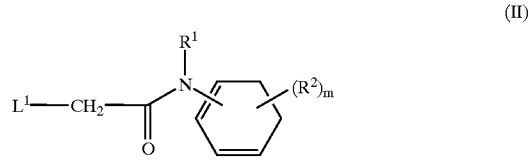

(II)

in which $R^1$ represents an alkyl, alkoxyalkyl or cycloalkyl group; $R^2$ each independently represent an alkyl or alkenyl group, m represents zero or an integer from 1 to 6, and $L^1$ represents a hydroxy group or a leaving group selected from alkyl- and arylsulfonyl, alkyl- and arylsulfonyloxy, and perfluoroalkylsulfonyloxy groups.

13. A herbicidal composition comprising at least one compound according to claim 1 and at least one agronomically acceptable carrier.

14. A composition according to claim 13 comprising at least two carriers, at least one of which is a surface-active agent.

15. A method of combating undesired plant growth at a locus which comprises applying to the locus a herbicidally effective amount of a compound described in claim 1.

16. A method of combating undesired plant growth at a locus which comprises applying to the locus a herbicidally effective amount of a composition according to claim 13.

* * * * *